United States Patent
Volfkovich et al.

(10) Patent No.: US 6,298,711 B1
(45) Date of Patent: Oct. 9, 2001

(54) POROSIMETER

(75) Inventors: Yury Mironovich Volfkovich; Igor Alexandrovich Blinov; Valentin Evseevich Sosenkin; Venedikt Venedictovich Kulbachevsky, all of Moscow (RU)

(73) Assignee: Porotech, Inc., Thornhill (CA)

( * ) Notice: Subject to any disclaimer, the term of this patent is extended or adjusted under 35 U.S.C. 154(b) by 0 days.

(21) Appl. No.: 09/341,096
(22) PCT Filed: Apr. 8, 1999
(86) PCT No.: PCT/RU99/00108
  § 371 Date: Jul. 2, 1999
  § 102(e) Date: Jul. 2, 1999
(87) PCT Pub. No.: WO00/62037
  PCT Pub. Date: Oct. 19, 2000

(51) Int. Cl.$^7$ ................................. G01N 15/08
(52) U.S. Cl. ............................................. 73/38
(58) Field of Search .................................... 73/38

(56) References Cited

FOREIGN PATENT DOCUMENTS

| 201753 | * | 11/1966 | (RU) | ................................... | 73/38 |
| 543852 | | 1/1977 | (RU) | ................................... | 73/38 |
| 1038836 | * | 8/1983 | (RU) | ................................... | 73/38 |
| 1485072 | * | 6/1989 | (RU) | ................................... | 73/38 |

OTHER PUBLICATIONS

Arthur W. Adamson, "Physical Chemistry of Surfaces", Third Editions, pp. 616–623, New York, 1976.

* cited by examiner

*Primary Examiner*—Daniel S. Larkin
(74) *Attorney, Agent, or Firm*—Jacobson Holman, PLLC

(57) ABSTRACT

A porosimeter for investigating physicochemical properties of materials and articles, in particular for investigation of a structure of porous bodies, including a scale, a clamping device for bringing into contact standard and test porous samples, the samples containing wetting liquid in its pores, and an automatic manipulator. The automatic manipulator includes a body, a frame, a motor connected with the frame by a transmission, the motor having pushers and a support. The clamping device for bringing the standard and test porous samples into contact with each other includes a drying device connected with the body, and yokes.

10 Claims, 5 Drawing Sheets

POROSIMETER

BACKGROUND OF THE INVENTION

1. Field of the Invention

The present invention pertains generally, to devices for investigation of physicochemical properties of materials and articles, in particular to devices for investigation of the structure of porous bodies.

2. Description of Related Art Including Information Disclosed Under 37 CFR 1.97 and 1.98

Devices for investigation of the porous structure of samples are known.

Generally, they employ a method of nonwettable liquid intrusion into pores of a test sample namely mercury, and are known as mercury porosimeters (H. L. Ritter, L. C. Drake, Ind. Eng. Chem. Analit. Ed., 17, 787, 1945; SU Inventors Certificate No. 104315, 1952 G 01 (15/08).

The mercury porosimeters, which are the most widespread porosimetric devices, measure distribution of pores by the samples' radii within the pore size range from 2 to $10^5$ nm.

However, measurements accomplished within the pore-size range from 2 to 7 nm require applying very high pressure to intrude mercury into the samples pores which is up to 4000 ATM and which involves a complicated device.

Under pressures of thousands ATM, deformation and destruction of most samples measured, especially plastic ones, takes place.

Besides, it is impossible to use mercury porosimeters for investigation of substances, which chemically react with mercury (amalgamation).

Also, when mercury porosimeters are used, the value of angle of wetting by mercury for most of the samples measured is not known. However, this value is used for computation of radii of pores measured.

In practice, various materials are measured when some mean value of this angle of wetting issued which entails significant errors in measurement.

Of great importance when employing mercury porosimeters is that it uses a substantial quantity of a highly toxic substance-mercury.

Also known in the art are devices for measurement of the porous structure of a substance by means of a method of capillary condensation, for instance an adsorption apparatus (A. W. Adamson, Physical Chemistry of Surface, John Wiley & Sons Publ., New York, 1976).

However, devices operating by the capillary condensation method provide sufficient accurate measurement of distribution of pores by radii only within the range from 1 (or –2) to 50 nm.

Also known is a device for measurement of characteristics of porous bodies by the method of standard porosimetry (USSR Inventor's Certificate No. 543852, 1975, GO1N15/08, Yu. M. Volfkovich, V. S. Bagotzky, J. Power Sources, 48 (1994) 327, 339).

The method is based on the fact that when pores of the test sample are filled with a wetting liquid or are free of the liquid, and when a determination of a quantity of liquid contained in its pores takes place, the test sample is brought into contact with the standard porous sample and when capillary equilibrium is achieved a measurement is performed of the quantity of the liquid in the test and standard samples.

The method consists in measurement, performed in the course of drying, of equilibrium dependency of a quantity of liquid in the test sample from its quantity in the standard sample while the samples are in contact with each other.

Proceeding from a curve plotted against results of measurements also from a known curve of distribution of pores by radii (porosimetric curve) for standard samples, it is determined under a specific procedure, porosimetric curves for the test samples.

By means of a mathematical processing of these curves other characteristics of a porous structure are obtained, for instance a specific surface.

A quantity of liquid in each porous sample is determined by means of weighing in the course of drying.

A device for measurement of the standard porosimetery consists of scales and a clamping device, wherein the test and standard porous samples are brought into contact.

The clamping device represents a body arranged as a beaker where the porous test and standard samples are placed. The samples are shut down by means of a draw plate having apertures through which drying of a stack is performed. A throw nut screwed on the body of the device clamps the samples to each other. To get one point on the porosimetric curve the stack is disassembled, the porous samples from the stack are laid out into individual bottles, and then after weighting, all samples are removed from the bottles, and the stack is reassembled anew in the clamping device. Then the next portion of the liquid is evaporated from the stack through drying, by means of a flow of dry gas or by vacuum, after which the stack of the porous bodies is disassembled, the porous bodies are laid out anew into the individual bottles, and then are weighed again.

To measure one porosimetric curve it is necessary depending on the required accuracy of measurement, to conduct this cycle of operations from fifteen up to fifty times. All of these stages are labor intensive and require a prolonged measurement process.

All the above known in the art decisions do not provide for a quickly obtaining accurate measurement results, and are not used for all ranges of pore radii. The process of measurement is a prolonged and laborious one.

BRIEF SUMMARY OF THE INVENTION

It is the primary object of the present invention to provide a porosimeter—a device for investigation of physicochemical properties of materials and articles, in particular for investigation of the structure of porous bodies.

It is another object of this invention to provide a porosimeter for investigation of the structure of porous bodies which permits in a fast manner and in an automatic operating mode to perform measurements within the maximum broad ranges of radii of pores for test samples of any chemical nature and strength.

Yet another object of the invention is to provide a porosimeter for investigation of the structure of porous bodies, which enables to increase the accuracy of measurements.

It is still another object of this invention to provide a porosimeter for investigation of the structure of porous bodies to define a greater quantity of information, including a specific surface, statistic characteristics of form and size of pores, marginal angles of wetting, characteristics of swelling, characteristics of a structure of multi-component hydrophobic-hydrophilous porous bodies and other characteristics.

According to these and other objects, the porosimeter of the present invention, having a scale and a clamping device for bringing the standard and test porous samples into tight contact with each other, said samples containing a wetting liquid in their pores, comprises an automatic manipulator consisting of a body, a frame and a motor connected through a transmission with the frame, said frame being provided with pushers and a support, while the device for bringing into tight contact of the standard and test porous samples additionally comprises a drying device which is connected with the body, and yokes having apertures to provide contact between the porous samples, said yokes being arranged as having catchers.

The drying device is preferred to be a cylindrical chamber with a bottom containing apertures, while a beaker having an outlet pipe is coaxially fixed inside of the chamber, said beaker being disposed by its open end towards the chamber's bottom, and having a clearance between an external surface of the beaker and an internal cylindrical surface of the chamber.

It is preferred that the yokes be cylindrical beakers entering each other and be provided with spring shock absorbers, spring washers and a ring-shaped slot arranged in the bottom of a yoke.

It is expedient that in the porosimeter for investigation of physicochemical properties of the materials and articles catchers are resilient and constituting balls which are spring-loaded by resilient plates, said balls possessing different pressing force to press tight the yokes to each other and to the drying chamber the less rather than the greater diameter of the yoke, while the balls are to be accomplished as possessing ability to enter respective grooves arranged in the yokes and in the drying chamber.

It is useful that in the porosimeter for investigation of physicochemical properties of the materials and articles and the transmission is a screw with a possibility of forward transference along the threads of the frame.

It is advantageous that in the porosimeter for investigation of physicochemical properties of the materials and articles, the pushers are rods fixed on the frame in a horizontal plane and directed towards the central axis of the yokes, while the distance from the yokes' axis to the edge of the pushers is longer than the distance from the axis to the internal surface of a respective yoke, but smaller than the distance from the axis to its outer surface.

It is advantageous that in the porosimeter for investigating physicochemical properties of the materials and articles, the support of the frame is a plate in the center of which there is arranged a cylindrical aperture having a diameter which is less than the outer diameter of the lower yoke.

It is useful that in the porosimeter for investigation of physicochemical properties of the materials and articles, a tray for the yokes is formed by two horizontal disks, the centers of which are connected by a rod while a diameter of the upper disk is smaller than a diameter of the aperture in the support.

It is expedient also that in the porosimeter for investigation of physicochemical properties of the materials and articles, a bubbler contains a liquid which is similar to that contained in pores of the test and standard samples.

BRIEF DESCRIPTION OF THE DRAWINGS

In what follows the invention will be described in greater detail with reference to the accompanying drawing wherein.

DETAILED DESCRIPTION OF THE INVENTION

Figure 1:
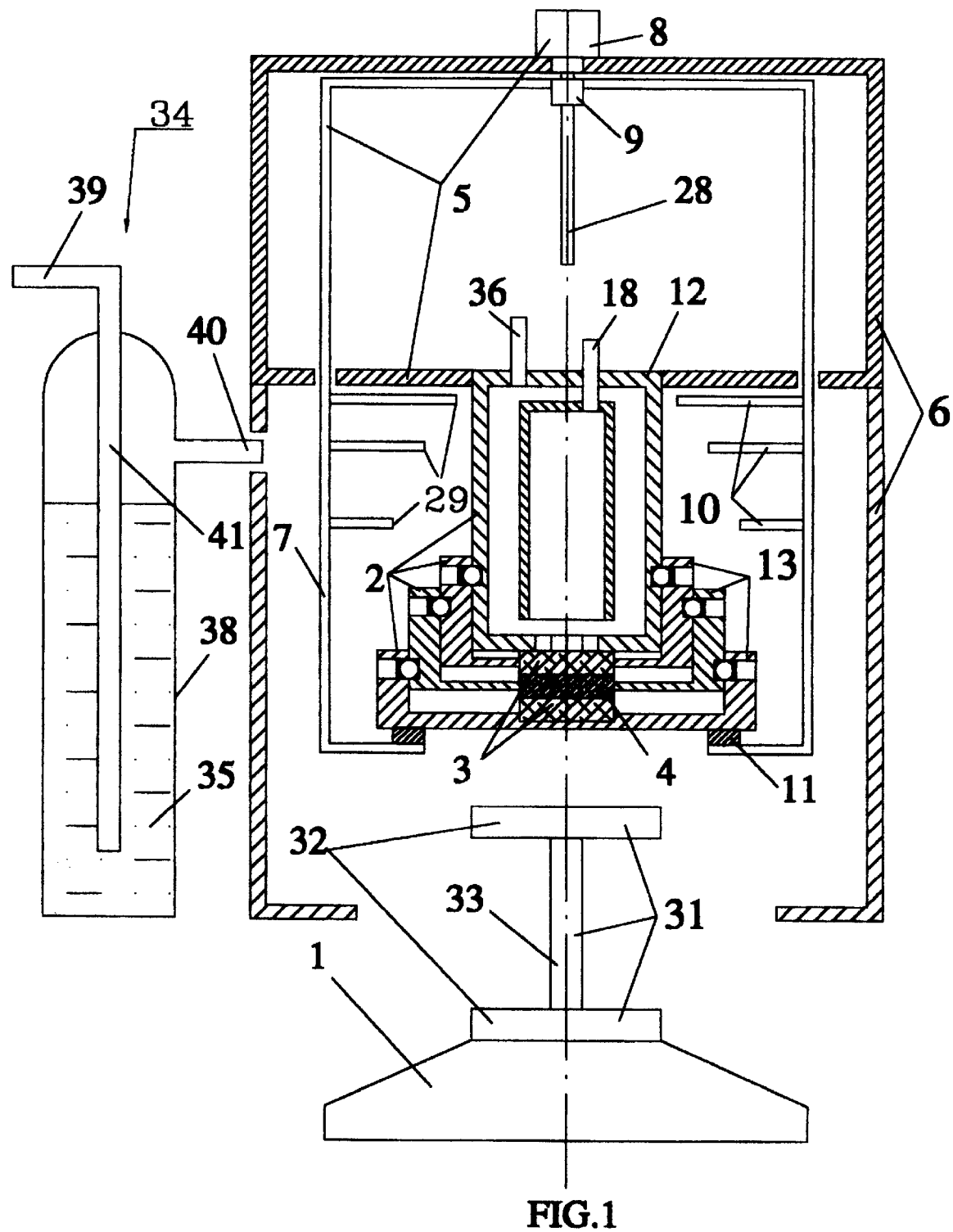
FIG. 1 shows a scheme of the porosimeter in accordance with the principles of the present invention.

The porosimeter for investigation of physicochemical properties of materials and articles comprises a scale 1 and a clamping device 2 for bringing together standard 3 and test 4 porous samples (FIG. 1), the porous samples 3, 4 containing a wetting liquid in its pores, an automatic manipulator 5 comprising a body 6, a frame 7 and a motor 8.

The motor 8 in its turn is connected by a transmission 9 with the frame 7.

The frame 7 further is provided with pushers 10 and a support 11.

The clamping device 2 for brining porous samples into contact comprises a drying device 12, connected with the body 6, and yokes 13 provided with through holes 14 arranged therein for provided the possibility of contact between neighboring porous samples.

The yokes 13 are provided with catchers 15 for fastening the yokes to each other and to the drying device 12.

The porous samples 3, 4 are arranged in the yokes 13. A cylindrical chamber, generally designated by the reference numeral 12, has a perforated bottom 16 with apertures 17, inside of which a beaker 19 is coaxially fastened, said beaker having an outlet pipe 18, which is in a preferred embodiment of the drying device 12.

The beaker 19 by its open end is fastened to the bottom of the chamber 12.

A clearance, generally designated by the reference numeral 20, is arranged between the perforated bottom of the chamber 12 and an edge of the beaker 19.

A clearance 21 is arranged between an outer cylindrical surface of the chamber 19 and an internal cylindrical surface of the chamber 12.

The catchers 15 are in the form of balls 23 which are spring-loaded by resilient plates 22 and which enter respective grooved slots 24 arranged on the yokes 13 and in the drying device 12.

To provide different exertion of removal: 0.5 kgf for the lower yoke-beaker, 1.0 kgf for the middle yoke-beaker, and 1.5 kgf for the upper yoke-beaker, the plate 22 have different thickness: 0.1 mm (for the lower yoke-beaker); 0.2 mm and 0.3 mm (for the upper yoke-beaker).

Spring shock absorbers 25, formed by steel plates, are fastened to the internal side of the bottom of the lower and middle yokes-beakers 13.

The yokes are fitted with spring washers 26 pressing down porous materials to its bottom to provide safe fastening of a sample to the yoke 13.

A ring-shaped slot 27 for fitting of a porous sample is arranged in the bottom of the yoke 13.

To make it possible to perform transformation of a rotary motion of the motor into a forward motion of the frame 7 the transmission 9 connecting the engine 8 with the frame 7 is formed by a screw 28.

To provide guaranteed pressing of the pushers 10 onto corresponding yokes the pushers are formed by rods directed towards a central axis of the yokes and fixed on the frame 7, while a distance from the axis to an edge 29 of the pusher 10 is greater than a distance from the axis to the internal surface of a corresponding yoke, but is smaller than a distance from the axis to its outer surface.

A cylindrical aperture 30 of a diameter which is smaller than the outer diameter of the lower yoke 13 is arranged on the support of the frame, formed by the plate 22, for the purpose of providing a sufficiently large surface of contact between the support 11 and the lower yoke 13 to achieve safe pressing between all of the porous samples.

To prevent the support 11 from letting down the lower yoke 13 onto a pan of scales 1 during forward motion of the frame 7, a post 31 for the yoke 13 is formed by two horizontally disposed discs 32 of which the centers are connected by means of a rod 33, while a diameter of the upper disc is smaller than that of the aperture 30 disposed in the support.

A bubbler 34 is arranged in the porosimeter to feed moistened gas inside the body 6, while the bubbler 34 contains the liquid 35 which is similar to that in the pores of the test and standard samples, the arrangement serving the purpose of maintaining the moistened gas atmosphere inside the body 6 of the porosimeter, said atmosphere providing a slower drying of the samples at the beginning of the measurement process, and providing the possibility of measurement of very large pores.

The cylindrical chamber 12 comprises, apart from the pipe 18 destined for entry of dry gas, also a pipe 36 for its discharge.

Each of the yokes 13 installed in the chamber 12, is provided with the through hole 14 arranged in the bottom thereof for the purpose of providing for contact between the neighboring samples, but the lower yoke, instead of having a through hole, is hollow 37.

Elimination of the through hole from the lower yoke is arranged to dry all samples only from above, that is from where it is fed the dry gas. Under this arrangement it is possible to only control the process of drying the porous samples.

The body 38 of the bubbler 34 is formed by a tabulated form, and comprises an inlet 39 and outlet 40 pipes.

To feed dry gas inside the bubbler 34, a tube 41 is arranged as an extension of the pipe and through this tube gas is fed downward to the bubbler 34 and then as the bubbler is saturated with liquid vapors, rising upward, moistened gas is fed inside the body 6 of the porosimeter.

Each standard sample is a ceramic porous disk of a diameter of 2 cm and a thickness of 1.5 mm. The standard samples are formed having pores with radii in the range from 1 to $10^5$ nm.

The porosimeter comprising such standard samples enables investigation of the porous structure of the test samples within the same range of the pore radii.

Figure 5:
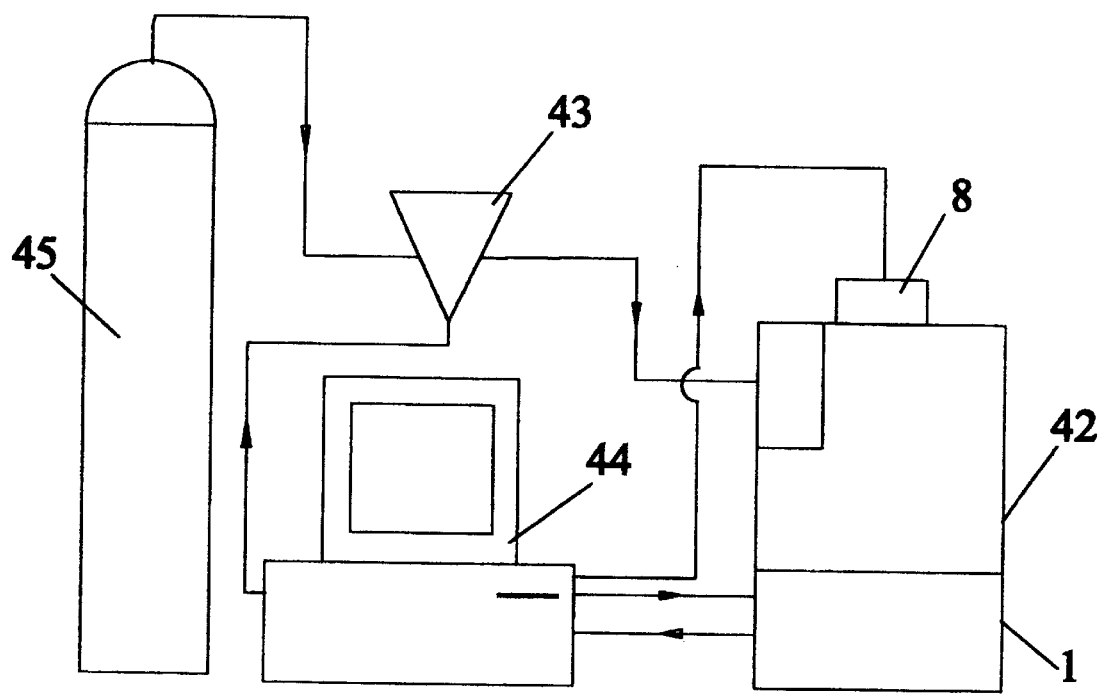
FIG. 5 shows one more embodiment in accordance with the principles of the present invention, which is a block diagram of a complete porosimeter installation.

Still another embodiment of the porosimeter in accordance with the principles of the present invention, is shown in a block-diagram of the invention (FIG. 5).

FIG. 5 shows a diagram of the invention without a bubbler. The invention comprises a mechanical block 42, which is the porosimeter of the present invention and a diagram of which is shown in FIG. 1, an electric motor 8 and an electronic scale 1 of the Sartorius A 200S brand provided with a microprocessor, and also an electromagnetic valve-regulator 43 of the rate of feeding dry gas into drying chamber 12, a personal computer 44 and a gas cylinder 45 with dry gas.

The installation functions as follows:

In a position when the porosimeter begins its performance (FIG. 1) the porous samples 3, 4 are in contact with each other, the yokes 13 are inserted one into another, and the upper one of the yokes is put in the drying chamber 12, while the pushers 10 are arranged above the yokes. The upper part of the frame 7 is connected by means of the transmission 9 with the motor 8, which is arranged on the body 6.

The porosimeter functions in the following manner:

The motor 8 is switched on to disassemble the stack of porous samples, said motor 8 through the transmission 9 lets down the frame 7 with the pushers 10 and the support 11, thus releasing the yokes 13 with the porous samples 3, 4.

The lower group of pushers, while pressing onto the upper surface of the lower yoke disconnects it from a neighboring above yoke, and the lower (first) yoke descends onto the scale 1.

Figure 2:
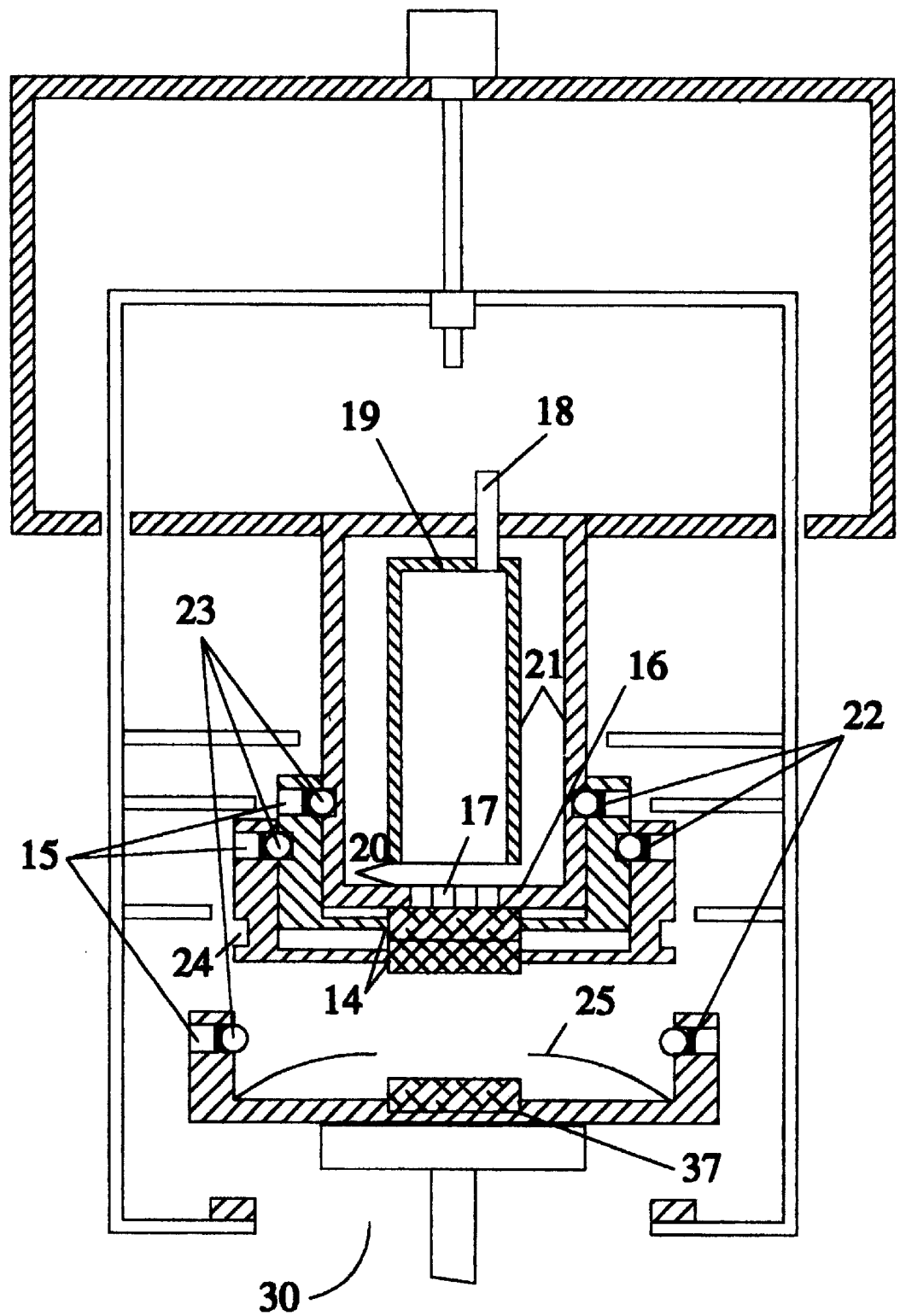
FIG. 2 shows a scheme of the porosimeter in the position of weighing of the lower yoke charged with a sample in accordance with the principles of the present invention.

FIG. 2 shows a diagram of the process of weighing the lower (first) yoke with the sample.

After that the motor 8 is shut down, and a mass of the lower (first) porous sample with the yoke is measured.

Figure 3:
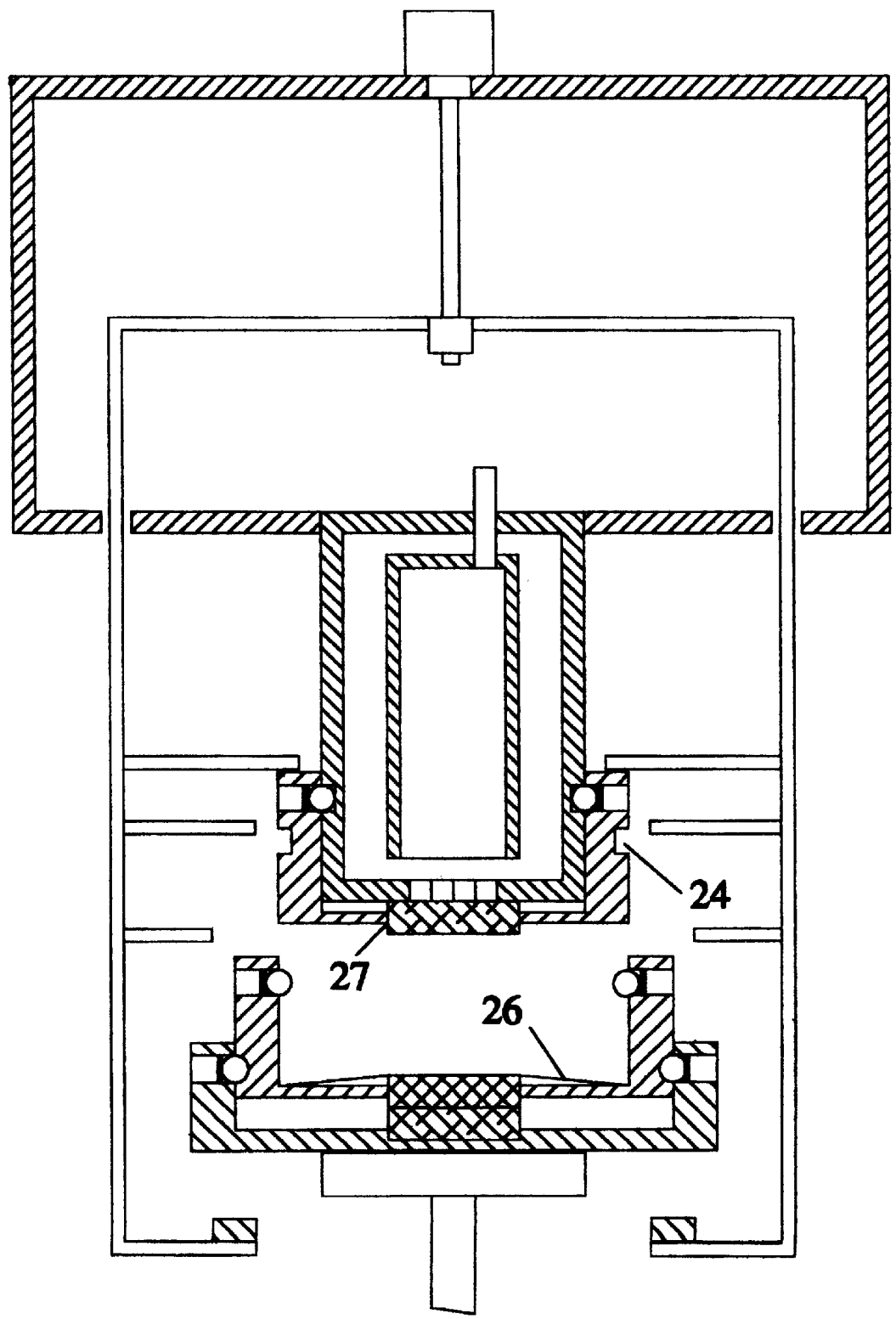
FIG. 3 shows a scheme of the porosimeter in the position of weighting of the two lower yokes charged with samples in accordance with the principles of the present invention.

Then after fixation of the mass the motor 8 is switched on, the frame 7 goes lower, the second (disposed above the first one) group of pushers goes into action disconnecting the second yoke with the porous sample from a neighboring above yoke, and the second from bottom yoke descends onto the scale 1. This yoke lies down on the first yoke which is already on the scale 1 (FIG. 3).

The motor 8 is shut down and an overall mass of the first and second porous bodies with their yokes is measured.

Figure 4:
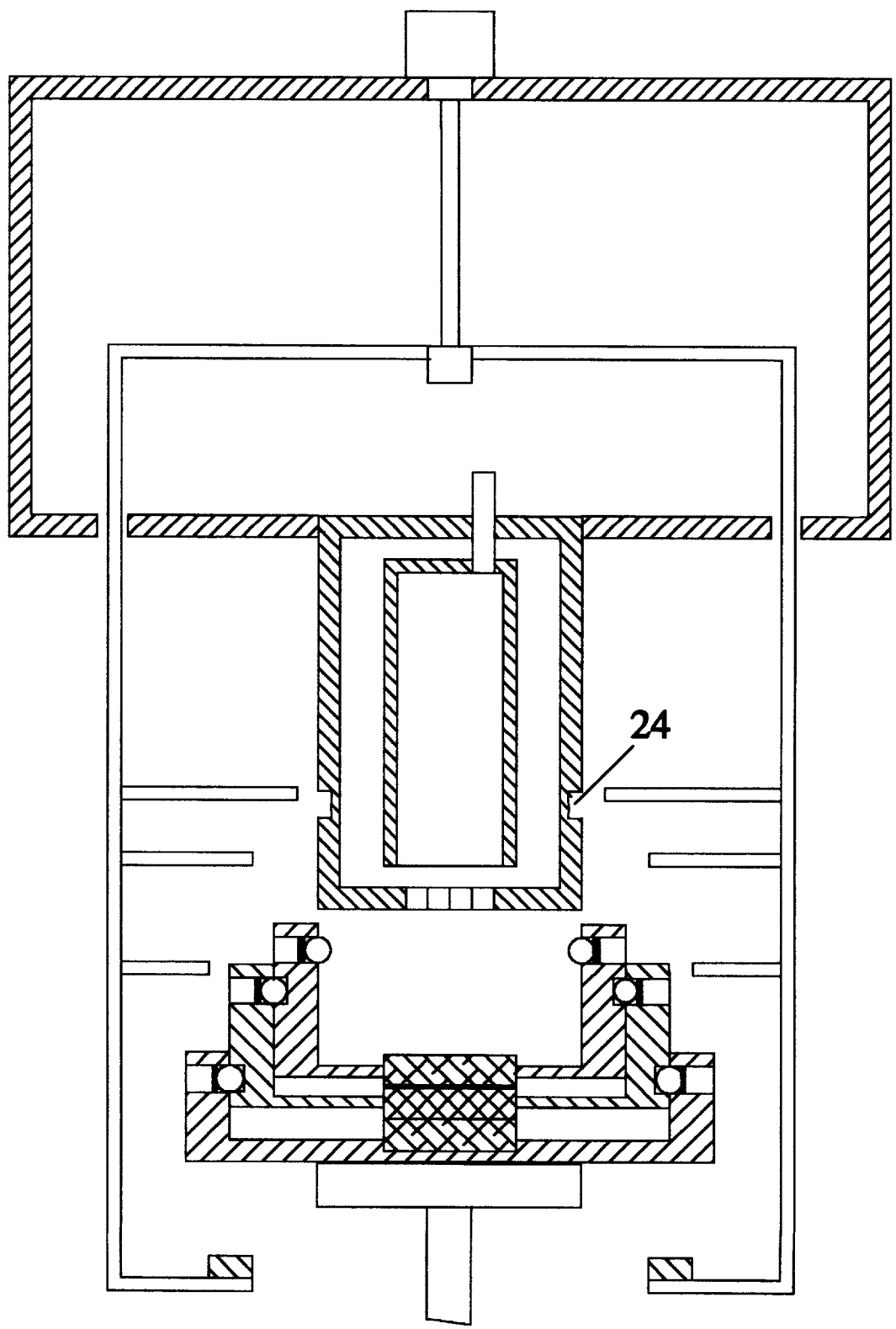
FIG. 4 shows a scheme of the porosimeter in the position of weighing of the three yokes charged with samples in accordance with the principles of the present invention.

In much the same way, all yokes with the porous samples are lowered down on the scale 1 (FIG. 4).

Then after measurement of the mass of all porous samples, a stack of the porous samples is assembled.

To achieve this, the direction of rotation of the motor 8 is reversed. The frame 7 begins to move upward.

The support 11 lifts the yokes 13 lying on the scale and puts them in the order one upon another while the extreme upper yoke 13 is put on the drying device 12 (FIG. 1).

The yokes are fastened to each other and to the drying device 12 by means of the catchers 15. Next follows a stage of drying the stack of the porous samples which is accomplished in the following manner: dry gas is fed in the drying device 12 which passes over the porous samples resulting in evaporation of liquid which in turn is evacuated as vapor together with gas from the drying device 12.

As a result of the measurement the current volumes of the standard and test porous samples with the yokes are obtained.

To obtain the volumes of liquid (moisture content) contained in pores of each of the samples at the given stage of measurement, the masses of the yokes and the dry porous samples are substracted from masses of current volumes.

The moisture contents of the standard samples is determined, when using their, known in advance, pore-radii distribution curves (porosimetric curves) and the current pores-radius.

When during the drying process the capillary equilibrium conditions are observed, then this pores' radius equals the current pores' radius for all tested samples.

The process of measurement is continued until complete evaporation of liquid from all tested samples is achieved.

As a result, the moisture content of the tested samples compared to the moisture content of the standard samples is obtained.

Known in advance porosimetric curves for the standard samples are obtained under a definite method as compared to the porosimetric curves for the tested samples, and also other parameters of the porous structure of the tested samples, for instance value of the specific surface.

The principle of operation of the embodiment of the installation shown in FIG. 5 is as follows:

All pores of the tested samples are vacuum saturated. After that these samples are inserted into the yokes 13—beakers which are fastened to the drying device 12. Dry gas from the cylinder 45 is fed through the electromagnetic valve 43 into the drying chamber 12.

In the process of drying values of the masses of the test and standard samples are introduced into a computer 44 which, under a special program, controls the electric motor 8 and the electromagnetic valve 43.

This program is compiled in such way as, on one side, sufficient accuracy of obtained characteristics of the porous structure is provided which requires a not so fast drying process and hence a not so high rate of feeding gas into the porosimeter, while on the other side time of measurements is reduced which should not be prolonged.

Thus optimization of the process of measurements is provided.

What is claimed is:

1. A porosimeter for investigating physicochemical properties of materials and articles of a porous body structure, said porosimeter comprising a scale, a clamping device for bringing standard and test porous samples together, said samples containing a wetting liquid, an automatic manipulator, said manipulator being constructed and arranged to define at least a body, a frame, and a motor connected by a transmission with the frame, said frame comprising a plurality of pushers and a support, the clamping device including a drying device connected with the body, and yokes, inside of which apertures are arranged, while the yokes are fitted with catchers for fastening the yokes to each other and to the drying device.

2. A porosimeter as defined in claim 1, wherein said drying device includes a cylindrical chamber with a bottom having openings, said cylindrical chamber being constructed and arranged to define a coaxially fastened beaker provided with an outlet pipe, said beaker having an open end located at a bottom of the chamber and defining a clearance arranged between the open end of the beaker and the bottom of the chamber, and with another clearance defined between an outer surface of the beaker and an inner cylindrical surface of the chamber.

3. A porosimeter as defined in claim 1, wherein the yokes comprise spring absorbers.

4. A porosimeter as defined in claim 1, wherein the yokes comprise spring washers.

5. A porosimeter as defined in claim 1, wherein a circular slot is arranged in the bottom of the yokes.

6. A porosimeter as defined in claim 1, wherein the catchers are resilient and spring-loaded by resilient plates, said catchers pressing the yokes against each other and against the drying device with different force.

7. A porosimeter as defined in claim 1, wherein the transmission includes a screw to be able to move forward along the frame.

8. A porosimeter as defined in claim 1, wherein the pushers include rods fastened onto the frame in a horizontal plane and directed to a central axis of the yokes while a distance from an axis of the yokes to a ridge of the pusher is greater than the distance from the axis to an inner surface of the corresponding yoke but is shorter than the distance from the axis to an inner surface.

9. A porosimeter as defined in claim 1, wherein the support of the frame includes a plate in a center having a cylindrical hole with a diameter smaller than an outer diameter of the yokes.

10. A porosimeter as defined in claim 9, wherein a stand for the yokes is arranged on the scale, said stand includes two horizontal discs, the centers of which are connected by a rod, while the diameter of the upper disc is smaller than a diameter of the hole in the support.

* * * * *